United States Patent [19]

Karrer

[11] Patent Number: 5,166,153

[45] Date of Patent: * Nov. 24, 1992

[54] BISACYLETHYLAMINES

[75] Inventor: Friedrich Karrer, Zofingen, Switzerland

[73] Assignee: Ciba-Geigy Corporation, Ardsley, N.Y.

[*] Notice: The portion of the term of this patent subsequent to May 19, 2009 has been disclaimed.

[21] Appl. No.: 515,001

[22] Filed: Apr. 24, 1990

[30] Foreign Application Priority Data

Apr. 27, 1989 [CH] Switzerland ............... 1599/89

[51] Int. Cl.$^5$ ............... C07C 271/02; C07D 265/30; C07D 31/50; C07D 31/33; A61K 31/325; A61K 31/505

[52] U.S. Cl. ............... 514/237.5; 514/212; 514/227.5; 514/247; 514/256; 514/255; 514/330; 514/365; 514/372; 514/374; 514/378; 514/399; 514/406; 514/423; 514/482; 514/486; 540/607; 544/58.4; 544/168; 544/224; 544/335; 544/406; 548/200; 548/214; 548/215; 548/240; 548/236; 548/237; 548/248; 548/341; 548/378; 548/538; 548/540; 546/226; 560/26; 560/27

[58] Field of Search ............... 560/26, 27; 514/482, 514/486, 237.5, 212, 227.5, 247, 256, 255, 330, 365, 372, 374, 378, 399, 406, 423; 544/168, 58.4, 224, 335, 406; 540/607; 546/226; 548/200, 214, 215, 240, 236, 237, 248, 341, 378, 538, 540

[56] References Cited

U.S. PATENT DOCUMENTS

| | | | |
|---|---|---|---|
| 4,080,470 | 3/1978 | Karrer | 514/482 |
| 4,215,139 | 7/1980 | Fischer et al. | 514/482 |
| 4,413,010 | 11/1983 | Zurflüh | 514/482 |
| 4,555,405 | 11/1985 | Böger et al. | 514/482 |
| 4,608,389 | 8/1986 | Kisida et al. | 514/482 |
| 4,745,128 | 5/1988 | Ujv ati et al. | 514/482 |
| 4,820,860 | 4/1989 | Wissmann et al. | 560/27 |

FOREIGN PATENT DOCUMENTS 0129513 12/1984 European Pat. Off. .
0350688 1/1990 European Pat. Off. .
3320534 12/1983 Fed. Rep. of Germany .
3334983 4/1984 Fed. Rep. of Germany .
2084574 4/1982 United Kingdom .

Primary Examiner—Johann Richter
Attorney, Agent, or Firm—Kevin T. Mansfield; Edward McC. Roberts

[57] ABSTRACT

Novel N-acylated 2-[4-(halophenoxy)-phenoxy]-ethylcarbamic acid esters of formula I

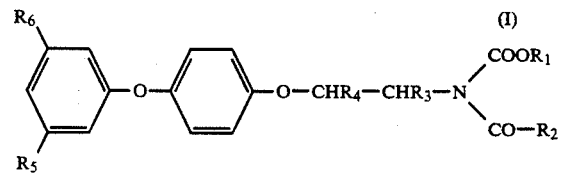

wherein
$R_1$ is $C_1$-$C_8$alkyl or $C_3$-$C_5$alkenyl,
$R_2$ is $C_1$-$C_8$alkyl, $C_1$-$C_8$alkoxy, —CO—$R_7$ or —NR$_8$R$_9$,
$R_3$ and $R_4$ independently of one another are hydrogen or methyl,
$R_5$ is chlorine or fluorine,
$R_6$ is either the same substituent as $R_5$ or is hydrogen,
$R_7$ is $C_1$-$C_8$alkoxy or —NR$_{10}$R$_{11}$,
$R_8$ is $C_1$-$C_4$alkyl,
$R_9$ is $C_1$-$C_4$alkyl or
$R_8$ and $R_9$ together form a $C_4$-$C_6$alkylene chain which may be interrupted by oxygen, sulfur or —NCH$_3$—,
$R_{10}$ is hydrogen or $C_1$-$C_4$alkyl and
$R_{11}$ is hydrogen or $C_1$-$C_4$alkyl, benzyl, phenyl, or phenyl substituted by halogen or by methyl, or
$R_{10}$ and $R_{11}$ together form a $C_4$-$C_6$alkylene chain which may be interrupted by oxygen, sulfur or —NCH$_3$—;
their preparation, their use in pest control, and pesticidal compositions that contain those carbamic acid esters as active ingredient are disclosed.

9 Claims, No Drawings

BISACYLETHYLAMINES

The present invention relates to novel N-acylated 2-[4-(halophenoxy)-phenoxy]-ethylcarbamic acid esters, to their preparation, to their use in pest control and to pesticidal compositions that contain those carbamic acid esters as active ingredient. The N-acyl-2-[4-(halophenoxy)-phenoxy]-ethylcarbamic acid esters according to the invention correspond to formula I

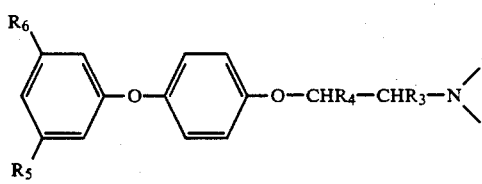

wherein
$R_1$ is $C_1$-$C_8$alkyl or $C_3$-$C_5$alkenyl,
$R_2$ is $C_1$-$C_8$alkyl, $C_1$-$C_8$alkoxy, —CO—$R_7$ or —$NR_8R_9$,
$R_3$ and $R_4$ independently of one another are hydrogen or methyl,
$R_5$ is chlorine or fluorine,
$R_6$ is either the same substituent as $R_5$ or is hydrogen,
$R_7$ is $C_1$-$C_8$alkoxy or —$NR_{10}R_{11}$,
$R_8$ is $C_1$-$C_4$alkyl,
$R_9$ is $C_1$-$C_4$alkyl or
$R_8$ and $R_9$ together form a $C_4$-$C_6$alkylene chain which may be interrupted by oxygen, sulfur or —$NCH_3$—,
$R_{10}$ is hydrogen or $C_1$-$C_4$alkyl and
$R_{11}$ is hydrogen or $C_1$-$C_4$alkyl, benzyl, phenyl, or phenyl substituted by halogen or by methyl, or
$R_{10}$ and $R_{11}$ together form a $C_4$-$C_6$alkylene chain which may be interrupted by oxygen, sulfur or —$NCH_3$—.

Halogen in the definition of $R_{11}$ is to be understood as meaning fluorine, chlorine, bromine or iodine, but preferably chlorine.

$C_1$-$C_8$alkyl groups may be straight-chain or branched. Examples of such radicals include methyl, ethyl, propyl, isopropyl or butyl and its isomers, and also the possible structural isomers of the $C_5$-$C_8$alkyls. Preferred alkyl groups contain not more than 4 carbon atoms. Methyl and ethyl are especially preferred.

$C_3$-$C_5$alkenyl groups in the definition of $R_1$ may be straight-chain or branched. The double bond of these groups is always separated from the bond to the oxygen atom by a saturated carbon atom. Examples are allyl, methallyl, 2-butenyl, 3-butenyl, 2-pentenyl, 3-pentenyl and 4-pentenyl.

Within the scope of the present invention, $C_1$-$C_8$alkoxy radicals in the definition of $R_2$ and $R_7$ are methoxy, ethoxy, propoxy, isopropoxy or the four butoxy isomers, or the possible structural isomers of the $C_5$-$C_8$alkoxy radicals. Special mention is made of the short-chain alkoxy groups having less than 5 carbon atoms. Of those groups, methoxy and ethoxy are preferred.

If the radical $R_6$ has a meaning other than hydrogen, i.e. is fluorine or chlorine, then, within the scope of the invention, $R_6$ is the same halogen atom as $R_5$.

If $R_8$ and $R_9$, or $R_{10}$ and $R_{11}$, together form a $C_4$-$C_6$alkylene chain which may be interrupted by oxygen, sulfur or —$NCH_3$—, then the groups —$NR_8R_9$ or —$NR_{10}R_{11}$ form a heterocycle that is bonded via the nitrogen atom. These heterocycles are based on the structures of, for example, pyrrolidine, piperidine, perhydroazepine, oxazolidine, thiazolidine, imidazolidine, pyrazolidine, perhydropyrimidine, morpholine, thiomorpholine, perhydropyridazine, isoxazolidine, isothiazolidine or piperazine.

Pesticidal ethylcarbamic acid derivatives have frequently been disclosed in the literature, but the spectrum of activity achieved with those substances is not completely satisfactory or is satisfactory only in some respects. Such compounds are known, for example, from U.S. Pat. Nos. 4,080,470, 4,215,139, 4,413,010, 4,555,405, 4,608,389 and 4,745,128, and from German Offenlegungsschriften DE-OS 3 320 534 and 3 334 983. There is therefore still a need for active ingredients of this class of substances with improved properties.

It has now been found that the compounds of formula I according to the invention are valuable active ingredients in pest control while being well tolerated by warm-blooded animals, fish and plants. The compounds according to the invention can be used especially against insects and arachnids which occur on useful plants and ornamentals in agriculture, especially in cotton, vegetable and fruit crops, in forestry, in the protection of stored goods and material stocks, and also in the hygiene sector, especially on domestic animals and productive livestock. They are effective against all or individual development stages of normally sensitive and also resistant species. Their action may manifest itself immediately in the death of the pests or only at a later date, for example at shedding, or in reduced oviposition and/or a reduced hatching rate. The above-mentioned pests include:

of the order Lepidoptera, for example,

Acleris spp., Adoxophyes spp., Aegeria spp., Agrotis spp., *Alabama argillaceae*, Amylois spp., *Anticarsia gemmatalis*, Archips spp., Argyrotaenia spp., Autographa spp., *Busseola fusca, Cadra cautella, Carposina nipponensis*, Chilo spp., Choristoneura spp., *Clysia ambiguella*, Cnaphalocrocis spp., Cnephasia spp., Cochylis spp., Coleophora spp., *Crocidolomia binotalis, Cryptophlebia leucotreta*, Cydia spp., Diatraea spp., *Diparopsis castanea*, Earias spp., Ephestia spp., Eucosma spp., *Eupoecilia ambiguella*, Euproctis spp., Euxoa spp., Grapholita spp., *Hedya nubiferana*, Heliothis spp., *Hellula undalis, Hyphantria cunea, Keiferia lycopersicella, Leucoptera scitella*, Lithocollethis spp., *Lobesia botrana*, Lymantria spp., Lyoneria spp., Malacosoma spp., *Mamestra brassicae, Manduca sexta*, Operophtera spp., *Ostrinia nubilalis*, Pammene spp., Pandemis spp., *Panolis flammea, Pectinophora gossypiella, Phthorimaea operculella, Pieris rapae*, Pieris spp., *Plutella xylostella*, Prays spp., Scirpophaga spp., Sesamia spp., Sparganothis spp., Spodoptera spp., Synanthedon spp., Thaumetopoea spp., Tortrix spp., *Trichoplusia ni* and Yponomeuta spp.;

of the order Coleoptera, for example,

Agriotes spp., Anthonomus spp., *Atomaria linearis, Chaetocnema tibialis*, Cosmopolites spp., Curculio spp., Dermestes spp., Diabrotica spp., Epilachna spp., Eremnus spp., *Leptinotarsa decemlineata*, Lissorhoptrus spp., Melolontha spp., Orycaephilus spp., Otiorhynchus spp., Phlyctinus spp., Popillia spp., Psylliodes spp., Rhizopertha spp., Scarabeidae, Sitophilus spp., Sitotroga spp., Tenebrio spp., Tribolium spp. and Trogoderma spp.; of the order Orthoptera, for example, Blatta spp., Blattella spp., Gryllotalpa spp., Leucophaea maderae, Locusta spp., Periplaneta spp. and Schistocerca spp.;

of the order Isoptera, for example,

Reticulitermes spp.; of the order Psocoptera, for example, Liposcelis spp.; of the order Anoplura, for example, Haematopinus spp., Linognathus spp., Pediculus spp., Pemphigus spp. and Phylloxera spp.; of the order Mallophaga, for example, Damalinea spp. and Trichodectes spp.;

of the order Thysanoptera, for example,

Frankliniella spp., Hercinothrips spp., Taeniothrips spp., *Thrips palmi, Thrips tabaci* and *Scirtothrips aurantii;* of the order Heteroptera, for example,

Cimex spp., *Distantiella theobroma,* Dysdercus spp., Euchistus spp., Eurygaster spp., Leptocorisa spp., Nezara spp., Piesma spp., Rhodnius spp., *Sahlbergella singularis,* Scotinophara spp. and Triatoma spp.;

of the order Homoptera, for example,

*Aleurothrixus floccosus, Aleyrodes brassicae,* Aonidiella spp., Aphididae, Aphis spp., Aspidiotus spp., *Bemisia tabaci,* Ceroplaster spp., *Chrysomphalus aonidium, Chrysomphalus dictyospermi, Coccus hesperidum,* Empoasca spp., *Eriosoma larigerum,* Erythroneura spp., Gascardia spp., Laodelphax spp., *Lecanium corni,* Lepidosaphes spp., Macrosiphus spp., Myzus spp., Nephotettix spp., Nilaparvata spp., Paratoria spp., Pemphigus spp., Planococcus spp., Pseudaulacaspis spp., Pseudococcus spp., Psylla spp., *Pulvinaria aethiopica,* Quadraspidiotus spp., Rhopalosiphum spp., Saissetia spp., Scaphoideus spp., Schizaphis spp., Sitobion spp., *Trialeurodes vaporariorum, Trioza erytreae* and *Unaspis citri;* of the order Hymenoptera, for example,

Acromyrmex, Atta spp., Cephus spp., Diprion spp., Diprionidae, *Gilpinia polytoma,* Hoplocampa spp., Lasius spp., *Monomorium pharaonis,* Neodiprion spp., Solenopsis spp. and Vespa spp.;

the order Diptera, for example,

Aedes spp., *Antherigona soccata, Bibio hortulanus, Calliphora erythrocephala,* Ceratitis spp., Chrysomyia spp., Culex spp., Cuterebra spp., Dacus spp., *Drosophila melanogaster,* Fannia spp., Gastrophilus spp., Glossina spp., Hypoderma spp., Hyppobosca spp., Liriomyza spp., Lucilia spp., Melanagromyza spp., Musca spp., Oestrus spp., Orseolia spp., *Oscinella frit, Pegomyia hyoscyami,* Phorbia spp., *Rhagoletis pomonella,* Sciara spp., Stomoxys spp., Tabanus spp., Tannia spp. and Tipula spp.;

of the order Siphonaptera, for example,

Ceratophyllus spp., *Xenopsylla cheopis;* of the order Acarina, for example,

Acarus siro, *Aceria sheldoni, Aculus schlechtendali,* Amblyomma spp., Argas spp., Boophilus spp., Brevipalpus spp., *Bryobia praetiosa,* Calipitrimerus spp., Chorioptes spp., *Dermanyssus gallinae, Eotetranychus carpini,* Eriophyes spp., Hyalomma spp., Ixodes spp., *Olygonychus pratensis,* Ornithodoros spp., Panonychus spp., *Phyllocoptruta oleivora, Polyphagotarsonemus latus,* Psoroptes spp., Rhipicephalus spp., Rhizoglyphus spp., Sarcoptes spp., Tarsonemus spp. and Tetranychus spp.; and of the order Thysanura, for example,

*Lepisma saccharina.*

The use of the compounds according to the invention in the control of rice cicadas, for example of the families Delphacidae and Cicadellidae, such as *Nilaparvata lugens, Laodelphax striatellus* and *Nephotettix cincticeps,* has proved to be of particular importance. The compounds of formula I also exhibit excellent activity against the so-called "white-flies" of the family Aleyrodidae with the genera Bemisia and Trialeurodes, such as. *Bemisia tabaci* or *Trialeurodes vaporarium,* which are difficult to control. The compounds of formula I achieve very good action against fruit tree pests of the families Tortricidae and Olethreutidae, for example with the genera Cydia, Adoxophyes and Lobesia, for example with the species *Cydia pomonella, Adoxophyes orana* and *Lobesia botrana.* The control of pests that parasitise animals, especially domestic animals and productive livestock, includes especially ectoparasites, such as mites and ticks, e.g. *Boophilus microplus* and *Dermanyssus gallinae,* Diptera, e.g. *Lucilia sericata,* and fleas, e.g. *Ctenocephalides felis.*

In the target groups of pests, the compounds of formula I essentially bring about an inhibition of growth or of development in the various stages of development, so that the reduction in the pest attack is the result of disturbances in the development of the pests, especially a chemosterilising and ovicidal effect.

Because of their advantageous biological activity, special mention should be made of compounds of formula I wherein $R_1$ is $C_1$-$C_4$alkyl, $R_2$ is $C_1$-$C_4$alkyl, $C_1$-$C_4$alkoxy, $C_1$-$C_4$dialkyl amino, $C_1$-$C_4$alkoxycarbonyl or —$CONR_{10}R_{11}$, and $R_5$ and $R_6$ are both either fluorine or chlorine, or $R_5$ is chlorine or fluorine and $R_6$ is hydrogen, wherein $R_{10}$ is hydrogen or $C_1$-$C_4$alkyl and $R_{11}$ is hydrogen, $C_1$-$C_4$alkyl or phenyl, or $R_{10}$ and $R_{11}$ together form a $C_4$-$C_6$alkylene chain which may be interrupted by oxygen.

Of this group of preferred compounds, those compounds in turn are preferred wherein $R_2$ is $C_1$-$C_4$alkyl, $C_1$-$C_4$alkoxy, $C_1$-$C_4$alkoxycarbonyl, $C_1$-$C_2$dialkylamino, di-($C_1$-$C_4$alkyl)-aminocarbonyl or $C_4$-$C_6$alkyleneaminocarbonyl.

An especially preferred group of compounds of formula I comprises those compounds wherein $R_1$ is $C_1$-$C_4$alkyl, $R_2$ is $C_1$-$C_4$alkyl, $C_1$-$C_4$alkoxy, di-($C_1$-$C_2$alkyl)-aminocarbonyl or $C_1$-$C_4$alkoxycarbonyl, $R_3$ is methyl or hydrogen, $R_4$ is hydrogen, and $R_5$ and $R_6$ are fluorine or chlorine.

Preferred individual compounds according to the present invention are:

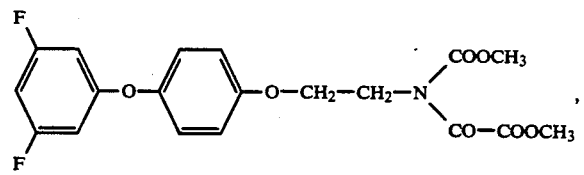

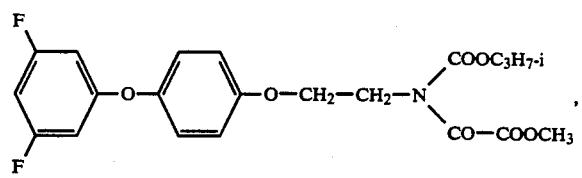

-continued
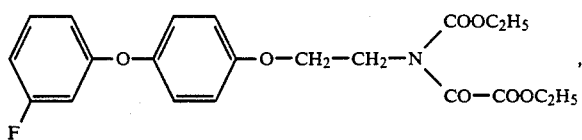
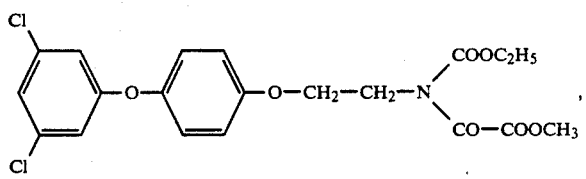
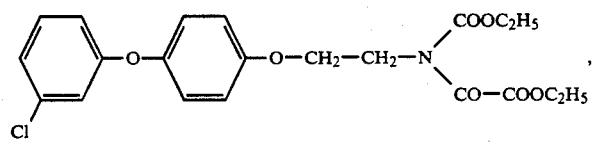
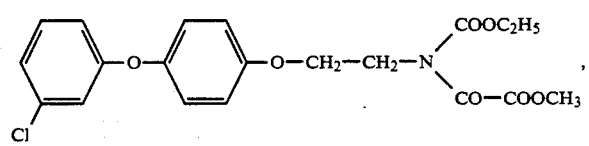
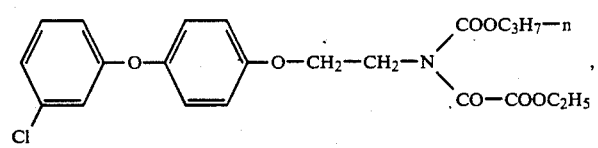
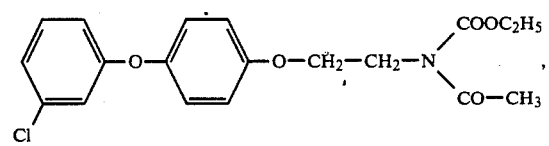
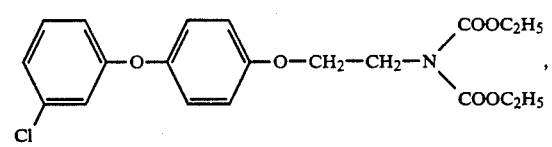
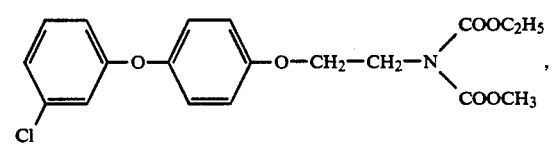
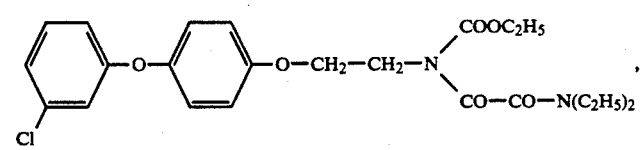
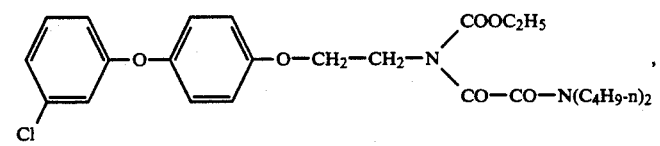

-continued

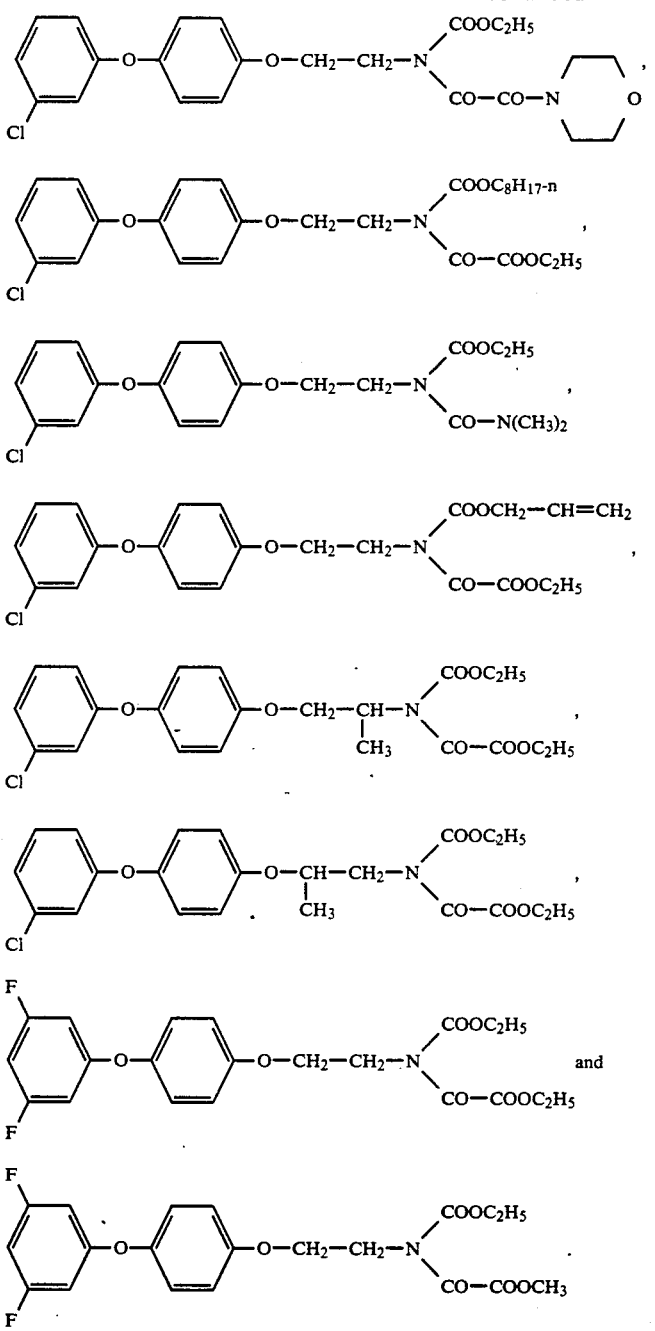

The compounds of formula I according to the invention can be prepared by methods that are known per se. For example, the compounds of formula I can be obtained by acylating a halophenoxyphenoxyethylcarbamic acid ester of formula II

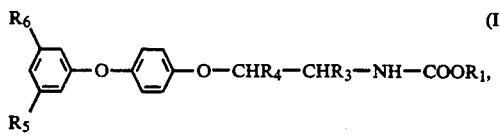

wherein $R_1$, $R_3$, $R_4$, $R_5$ and $R_6$ are as defined under formula I, with an acyl compound of formula III $$X\text{—}CO\text{—}R_2 \qquad (III),$$

wherein $R_2$ is as defined under formula I and X is chlorine, bromine, —O—CO—$R_2$ or —O—CO($C_1$-$C_4$alkyl).

The preparation process according to the invention is preferably carried out in the presence of a base. Suitable bases are both inorganic bases, such as alkali metal and alkaline earth metal carbonates or hydrogen carbonates, for example sodium carbonate, potassium carbonate, sodium hydrogen carbonate or potassium hydrogen carbonate, or alkali metal and alkaline earth metal hydrides, such as potassium hydride, sodium hydride or calcium hydride, and organic bases, such as tertiary amines, for example trialkylamines, such as triethylamine, diisopropylethylamine, pyridine, dimethylaminopyridine, 1,4-diazabicyclo[2.2.2]octane or 1,8-diazabicyclo[5.4.0]undec-7-ene; alkali metal alcoholates, such as sodium methanolate, sodium ethanolate or potassium tert-butanolate, or alkali metal alkyl compounds, such as butyllithium.

Advantageously, the reactions for the preparation of the compounds of formula I according to the invention are carried out in inert, aprotic organic solvents. Such solvents are hydrocarbons, such as hexane, heptane, cyclohexane, ligroin, benzene, toluene, xylene, mesitylene or Tetralin; chlorinated hydrocarbons, such as dichloromethane, chloroform, carbon tetrachloride, chlorobenzene, dichlorobenzene, trichloroethane or tetrachloroethane; ethers, such as diethyl ether, 1,2-dimethoxyethane, tetrahydrofuran or dioxane; nitriles, such as acetonitrile or propionitrile; dimethyl sulfoxide or sulfolane; or dialkylformamides, such as dimethylformamide or dimethylacetamide.

Depending on the choice of solvent and of the base that is optionally used, the reaction temperatures for the process according to the invention are generally from $-10°$ C. to the boiling point of the reaction mixture, usually from $0°$ C. to $+130°$ C. Preferred reaction temperatures are from $+20°$ C. to $+100°$ C. When highly reactive reagents, for example butyllithium, are used, the reaction temperature is preferably kept considerably lower, for example at from $-80°$ C. to $+20°$ C. The preferred range in that case is, for example, from $-70°$ C. to $0°$ C.

In a variant of the above process, the compounds of formula I wherein $R_2$ is the group $-CO-R_7$ can also be obtained by firstly reacting the carbamic acid ester of formula II with oxalic acid dichloride and then reacting the resulting intermediate of the formula

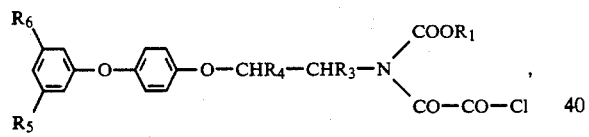

wherein $R_1$, $R_3$, $R_4$, $R_5$ and $R_6$ are as defined under formula I, with an alcohol or an amine of the formula

H—R$_7$, wherein $R_7$ is as defined under formula I, in the presence of a base.

Many of the starting materials of formulae II and III are known. Novel individual compounds falling within the scope of formulae II and III can be prepared by known methods. For example, the starting materials of formula II are obtained in simple manner by reacting a 2-[4-(halophenoxy)-phenoxy]ethylamine of formula IV

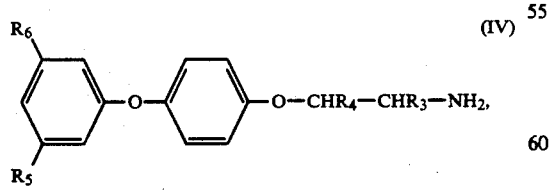

wherein $R_3$, $R_4$, $R_5$ and $R_6$ are as defined under formula I, with a haloformic acid ester of formula V Hal—CO—OR$_1$ (V), wherein $R_1$ is as defined under formula I and Hal is halogen, preferably bromine or chlorine, in the presence of a base. The compounds of formula II can also be prepared by reacting a phenoxyphenol of the formula

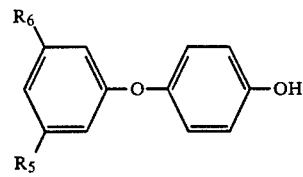

with a 2-haloethylcarbamic acid ester of the formula

Hal—CH(R$_4$)—CH(R$_3$)—NH—CO—OR$_1$ in the presence of a base, wherein $R_1$, $R_3$, $R_4$, $R_5$ and $R_6$ are as defined above and Hal is a halogen atom, preferably chlorine or bromine.

With the exception of the 1-methylethylamines of formula IVa

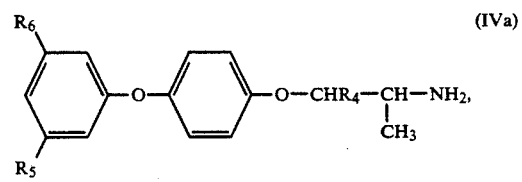

wherein $R_4$, $R_5$ and $R_6$ are as defined under formula I, the compounds of formula IV and V are known. The novel intermediates of formula IVa can be prepared in the following manner by reductive amination:

Scheme 1

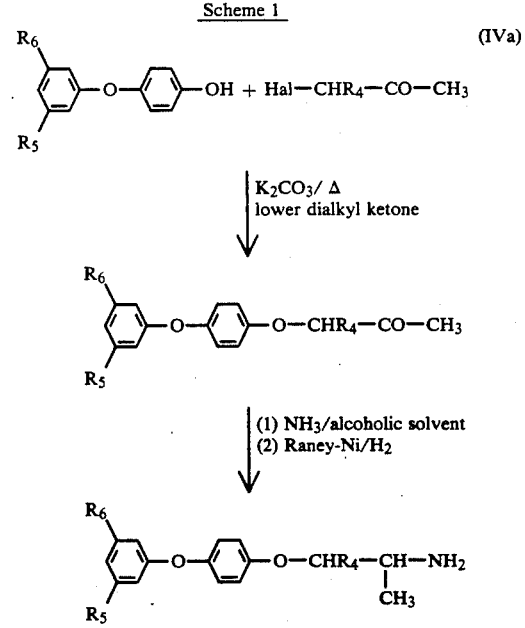

$R_4$, $R_5$ and $R_6$ are as defined under formula I; Hal is chlorine or bromine.

The compounds of formula IVa are novel, and the present invention relates also to those compounds and to a process for the preparation thereof.

The activity of the compounds of the invention and of the compositions containing them can be substantially broadened and adapted to prevailing circumstances by the addition of other insecticides and/or acaricides. Examples of suitable additives are organophosphorus compounds, nitrophenols and derivatives thereof, formamidines, ureas, carbamates, pyrethroids, chlorinated hydrocarbons and *Bacillus thuringiensis* preparations.

Especially advantageously, the compounds of formula I can also be combined with substances that effect an increase in pesticidal action. Examples of such compounds are inter alia: piperonyl butoxide, propynyl ethers, propynyl oximes, propynyl carbamates and propynyl phosphonates, 2-(3,4-methylenedioxyphenoxy)-3,6,9-trioxaundecane and S,S,S-tributylphosphorotrithioates.

The compounds of formula I are used in unmodified form or, preferably, together with the adjuvants conventionally employed in the art of formulation, and are therefore formulated in known manner e.g. into emulsifiable concentrates, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering or pouring, are chosen in accordance with the intended objectives and the prevailing circumstances.

The formulations, i.e. the compositions, preparations or mixtures containing the compound (active ingredient) of formula I or combinations of those active ingredients with other insecticides or acaricides and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used, e.g. for dusts and dispersible powders, are normally natural mineral fillers such as calcite, talcum, kaolin, montmorillonite or attapulgite. In order to improve the physical properties it is also possible to add highly dispersed silicic acids or highly dispersed absorbent polymers.

Suitable granulated adsorptive carriers are both porous types, for example pumice, broken brick, sepiolite or bentonite, and nonsorbent carriers such as calcite or sand. In addition, a great number of pregranulated materials of inorganic or organic nature can be used, e.g. especially dolomite or pulverised plant residues.

Depending on the nature of the compound of formula I to be formulated or the combinations of those compounds and other insecticides or acaricides, suitable surface-active compounds are non-ionic, cationic and-/or anionic surfactants having good emulsifying, dispersing and wetting properties. The term "surfactants" will also be understood as comprising mixtures of surfactants.

Both so-called water-soluble soaps and water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tall oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and generally contain a $C_8$–$C_{22}$alkyl radical, which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing about 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde.

Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols. Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxylower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described inter alia in the following publications:

"1985 International Mc Cutcheon's Emulsifiers & Detergents", Glen Rock, NJ, USA, 1985, H. Stache, "Tensid-Taschenbuch", 2nd edition, C. Hanser Verlag, Munich, Vienna, 1981, M. and J. Ash, "Encyclopedia of Surfactants", Vol. I–III, Chemical Publishing Co., New York, 1980–1981.

The pesticidal compositions usually contain 0.1 to 99%, preferably 0.1 to 95%, of the compound of formula I or combinations of that compound with other insecticides or acaricides, 1 to 99.9% of a solid or liquid adjuvant, and 0 to 25%, preferably 0.1 to 20%, of a surfactant. Whereas commercial products will preferably be formulated as concentrates, the end user will normally employ dilute formulations which contain considerably lower concentrations of active ingredient. Typical application concentrations are from 0.1 to 1000 ppm, preferably from 0.1 to 500 ppm. The rates of application per hectare are generally from 10 to 1000 g of active ingredient per hectare, preferably from 25 to 250 g/ha.

Preferred formulations have especially the following compositions (percentages are by weight):

Emulsifiable Concentrates active ingredient: 1 to 50%, preferably 5 to 30%
surface-active agent: 5 to 30%, preferably 10 to 20%
liquid carrier: 20 to 94%, preferably 50 to 85%

Dusts active ingredient: 0.1 to 10%, preferably 0.1 to 1%
solid carrier: 99.9 to 90%, preferably 99.9 to 99%

Suspension Concentrates active ingredient: 5 to 75%, preferably 10 to 50%
water: 94 to 24%, preferably 88 to 30%
surface-active agent: 1 to 40%, preferably 2 to 30%

Wettable Powders active ingredient: 0.5 to 90%, preferably 1 to 80%
surface-active agent: 0.5 to 20%, preferably 1 to 15%
solid carrier: 5 to 95%, preferably 15 to 90%

Granulates active ingredient: 0.5 to 30%, preferably 3 to 15%
solid carrier: 99.5 to 70%, preferably 97 to 85%.

The compositions may also contain further additives such as stabilisers, antifoams, preservatives, viscosity regulators, binders, tackifiers as well as fertilisers or other active ingredients for obtaining special effects.

The following Examples serve to illustrate the invention. They do not limit the invention.

EXAMPLE P1

N-Ethoxyoxalyl-2-[4-(3,5-difluorophenoxy)phenoxy]-ethylcarbamic acid ethyl ester

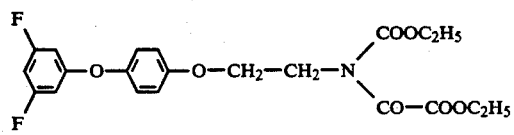

A solution of 8 g of oxalic acid monoethyl ester chloride in 10 ml of 1,2-dichloroethane is added dropwise at +80° C. within a period of 15 minutes, with stirring and under a nitrogen atmosphere, to a solution of 9.2 g of 2-[4-(3,5-difluorophenoxy)-phenoxy]-ethylcarbamic acid ethyl ester and 0.2 g of 4-dimethylaminopyridine in 70 ml of 1,2-dichloroethane. The mixture is then stirred at +80° C. for 15 hours. After cooling to room temperature, the reaction mixture is washed with water, 0.1N hydrochloric acid and then again with water and dried over sodium sulfate. The solvent is distilled off completely in vacuo. The resulting N-ethoxyoxalyl-N-2-[4-(3,5-difluorophenoxy)-phenoxy]-ethylcarbamic acid ethyl ester is purified by chromatography over silica gel (eluant: n-hexane/diethyl ether, 5:1) and then recrystallised from n-hexane with the addition of a small amount of ether. Colourless crystals of the title compound having a melting point of 73° C.–75° C. are obtained.

EXAMPLE P2

N-Methoxyoxalyl-2-[4-(3,5-difluorophenoxy)phenoxy]-ethylcarbamic acid ethyl ester

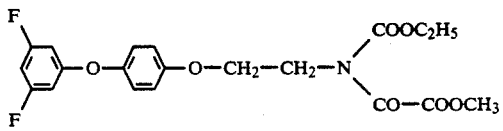

A solution of 8 g of oxalic acid monomethyl ester chloride in 10 ml of 1,2-dichloroethane is added dropwise at +80° C. within a period of 15 minutes, with stirring and under a nitrogen atmosphere, to a solution of 9.2 g of 2-[4-(3,5-difluorophenoxy)-phenoxy]-ethylcarbamic acid ethyl ester and 0.2 g of 4-dimethylaminopyridine in 70 ml of 1,2-dichloroethane. The mixture is then stirred at +80° C. for 15 hours. After cooling to room temperature, the reaction mixture is washed until neutral with water, 0.1N hydrochloric acid and then again with water and dried over sodium sulfate. The solvent is distilled off completely in vacuo. The resulting N-methoxyoxalyl-2-[4-(3,5-difluorophenoxy)-phenoxy]-ethylcarbamic acid ethyl ester is purified by chromatography over silica gel (eluant: n-hexane/diethyl ether, 5:1) and then recrystallised from n-hexane with the addition of a small amount of ether: colourless crystals having a melting point of 56° C.–58° C.

EXAMPLE P3

N-Ethoxyoxalyl-2-[4-(3,5-difluorophenoxy)phenoxy]-ethylcarbamic acid methyl ester

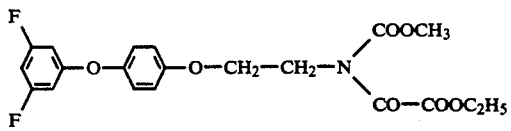

a) 21.3 g of potassium carbonate powder, 1.5 g of finely powdered potassium iodide and 16 g of 2-chloroethylcarbamic acid methyl ester are added to a solution of 17.1 g of 4-(3,5-difluorophenoxy)-phenol in 100 ml of dimethylformamide, and the reaction mixture is heated at +95° C. for 15 hours. The reaction mixture is then cooled, poured onto ice-water and extracted repeatedly with ether. The combined ether phases are washed with water and dried over sodium sulfate. The solvent is distilled off completely. The crude product is purified further by chromatography over silica gel (eluant: petroleum ether (40° C.–65° C.)/diethyl ether, 5:1), yielding 2-[4-(3,5-difluorophenoxy)-phenoxy]-ethylcarbamic acid methyl ester, $n^{21}_D$: 1.5394.

The following carbamic acid alkyl esters are prepared analogously from the corresponding 2-chloroethylcarbamic acid ethyl, isopropyl, n-propyl and allyl esters and 3,5-difluoro- or 3-chloro-phenoxy-phenols:

2-[4-(3,5-difluorophenoxy)-phenoxy]-ethylcarbamic acid isopropyl ester, $n^{21}_D$: 1.5243;

2-[4-(3-chlorophenoxy)-phenoxy]-ethylcarbamic acid methyl ester, $n^{20}_D$: 1.5719;

2-[4-(3-chlorophenoxy)-phenoxy]-ethylcarbamic acid ethyl ester, m.p.: 45° C.–46° C.;

2-[4-(3-chlorophenoxy)-phenoxy]-ethylcarbamic acid n-propyl ester, m.p.: 62° C.–63° C.;

2-[4-(3-chlorophenoxy)-phenoxy]-ethylcarbamic acid isopropyl ester, m.p.: 61° C.–62° C. and 2-[4-(3-chlorophenoxy)-phenoxy]-ethylcarbamic acid n-allyl ester, m.p.: 51° C.–52° C.

b) From the intermediates obtained according to a), the following end products according to the invention are obtained in a procedure as described in Example P1 using oxalic acid monomethyl ester chloride or oxalic acid monoethyl ester chloride:

N-ethoxyoxalyl-2-[4-(3,5-difluorophenoxy)-phenoxy]-ethylcarbamic acid methyl ester, $n^{20}_D$: 1.5230;

N-methoxyoxalyl-2-[4-(3,5-difluorophenoxy)-phenoxy]-ethylcarbamic acid isopropyl ester, $n^{21}_D$: 1.5152;

N-ethoxyoxalyl-2-[4-(3-chlorophenoxy)-phenoxy]-ethylcarbamic acid ethyl ester, $n^{20}_D$: 1.5396 and N-ethoxyoxalyl-2-[4-(3-chlorophenoxy)-phenoxy]-ethylcarbamic acid allyl ester, $n^{20}_D$: 1.5441.

EXAMPLE P4

N-Methoxyoxalyl-2-[4-(3-chlorophenoxy)-phenoxyl]-1-methylethylcarbamic acid ethyl ester

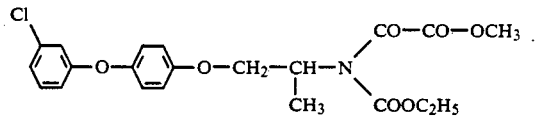

a) 32 g of powdered potassium carbonate and 2 g of finely powdered potassium iodide are added to a solution of 39.8 g of 4-(3-chlorophenoxy)-phenol in 250 ml of ethyl methyl ketone, and the mixture is heated to reflux temperature. 25 g of freshly distilled chloroacetone are added dropwise within a period of one hour, with stirring, and the mixture is then stirred at reflux temperature for a further 2 hours. After cooling, the reaction mixture is filtered, the solvent is distilled off in vacuo, and the crude product is filtered through silica gel, yielding pure, colourless 1-[4-(3-chlorophenoxy)-phenoxy]-2-propanone, $n^{20}_D$: 1.5788.

b) 51 g of 1-[4-(3-chlorophenoxy)-phenoxy]-2-propanone are dissolved in 510 ml of methanol in an autoclave, and 10 g of Raney nickel are added. 31 g of liquid ammonia are introduced, and then hydrogen gas is introduced under pressure. The reaction mixture is hydrogenated at 50 bar and +40° C.–45° C. for 2 hours. The reaction mixture is then filtered through diatomaceous earth and the solvent is distilled off completely in vacuo. The crude product is chromatographed over silica gel (eluant: diethyl ether/methanol, 9:1), yielding pure 2-amino-1-[4-(3-chlorophenoxy)-phenoxy]-propane in the form of a colourless, oily liquid, $n^{20}_D$: 1.5743.

c) A solution of 13.5 g of chloroformic acid ethyl ester in 20 ml of toluene is added dropwise at 20° C.–22° C. within a period of 30 minutes, with stirring, to a solution of 31.5 g of 2-amino-1-[4-(4-fluorophenoxy)-phenoxy]-pro pane, 20 g of diisopropylethylamine and 1.0 g of 4-dimethylaminopyridine in 120 ml of toluene. The mixture is then stirred at room temperature for 15 hours. For working up, the reaction mixture is poured onto 500 ml of ice-water and extracted three times with ether. The combined organic phases are washed twice with cold 1N hydrochloric acid and with water. After drying the organic solution over sodium sulfate, the solvent is distilled off and the crude product is purified by chromatography over silica gel (eluant: n-hexane/-diethyl ether, 5:1), yielding pure 2-[4-(3-chlorophenoxy)-phenoxy]-1-methylethylcarbamic acid ethyl ester in the form of a pale yellow, oily liquid; $n^{21}_D$: 1.5530.

d) A solution of 6.3 g of oxalic acid monomethyl ester chloride in 10 ml of 1,2-dichloroethane is added dropwise at +80° C. within a period of 20 minutes, with stirring and under a nitrogen atmosphere, to a solution of 9.0 g of 2-[4-(3-chlorophenoxy)-phenoxy]-1-methylethylcarbamic acid ethyl ester and 0.2 g of 4-dimethylaminopyridine in 50 ml of 1,2-dichloroethane. The mixture is then stirred at +80° C. for 17 hours. After cooling to room temperature, the reaction mixture is washed in succession with cooled saturated sodium hydrogen carbonate solution, with 0.1N hydrochloric acid and finally with water, and then dried over sodium sulfate. The 1,2-dichloromethane is distilled off completely in vacuo. The resulting N-methoxyoxalyl-2-[4-(3-chlorophenoxy)-phenoxy]-1-methylethylcarbamic acid ethyl ester can, if desired, be chromatographed over silica gel (eluant: n-hexane/dichloromethane, 3:1); $n^{20}_D$: 1.5443.

EXAMPLE P5

N-(Ethoxyoxalyl)-2-[4-(3-chlorophenoxy)phenoxy]-propylcarbamic acid ethyl ester

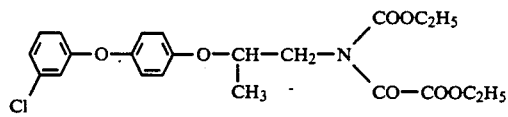

a) A solution of 15 g of potassium tert.-butoxide in 45 ml of dimethyl sulfoxide is added, with stirring and with slight external cooling, to a solution of 25.2 g of 3-chlorophenoxyphenol in 40 ml of dimethyl sulfoxide; 1.5 g of 18-Crown-6 are added, a solution of 28.3 g of 2-methylsulfonyloxypropylcarbamic acid ethyl ester in 30 ml of dimethyl sulfoxide is added dropwise at 15° C. within a period of one hour, and then the mixture is stirred firstly at 20° C.–22° C. for 5 hours and then at +55° C. for 19 hours. After cooling, the reaction mixture is poured onto ice-water and extracted repeatedly with ether, the combined ether phases are washed with water, and the solvent is distilled off. The crude product is purified further by chromatography over silica gel (eluant: diethyl ether/hexane, 1:9), yielding 2-[4-(3-chlorophenoxy)phenoxy]-propylcarbamic acid ethyl ester in the form of a pale yellow, viscous oil, $n^{20}_D$: 1.5500.

b) 4.3 g of oxalic acid monoethyl ester chloride are added dropwise at +80° C. within a period of 10 minutes, with stirring, to a solution of 5.5 g of 2-[4-(3-chlorophenoxy)phenoxy]-propylcarbamic acid ethyl ester and 0.2 g 4-dimethylaminopyridine in 50 ml of 1,2-dichloroethane. The mixture is then stirred at +80° C. for a further 25 hours. After cooling to room temperature, the reaction mixture is washed repeatedly with water and saturated sodium hydrogen carbonate solution and dried over sodium sulfate. The solvent is distilled off completely in vacuo. The N-(ethoxyoxalyl)-2-[4-(3-chlorophenoxy)-phenoxy]-propylcarbamic acid ethyl ester obtained as crude product is purified by chromatography over silica gel (eluant: diethyl ether/n-hexane, 1:6) and thus obtained in pure form as a viscous, oily liquid, $n^{20}_D$: 1.5303.

EXAMPLE P6

N-Ethoxycarbonyl-2-[4-(3-chlorophenoxy)phenoxy]-ethylcarbamic acid ethyl ester

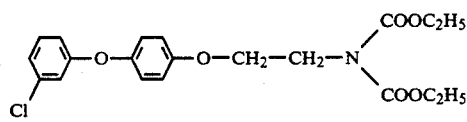

1.50 g of a 55% sodium hydride dispersion in mineral oil are washed repeatedly with n-hexane and suspended in 30 ml of tetrahydrofuran. To this suspension there is added dropwise at room temperature, with stirring, a solution of 11.5 g of 2-[4-(3-chlorophenoxy)-phenoxy]-ethylcarbamic acid ethyl ester in 30 ml of tetrahydrofuran, and the mixture is stirred at room temperature for a further 5 hours until the sodium hydride has reacted completely. Then a solution of 4.6 g of freshly distilled chloroformic acid ethyl ester in 10 ml of tetrahydrofuran is added dropwise at 0° C.-5° C. within a period of 10 minutes, and the mixture is stirred at room temperature for a further 50 minutes. The reaction mixture is then poured onto ice-water and extracted repeatedly with ether. The combined ether phases are washed twice with cold saturated sodium hydrogen carbonate solution and then with water and sodium chloride solution, the organic phase is dried over sodium sulfate, and the solvent is distilled off. The crude product is purified further by chromatography over silica gel (eluant: n-hexane/diethyl ether, 5:1), yielding N-ethoxycarbonyl-2-[4-(3-chlorophenoxy)-phenoxy]-ethylcarbamic acid ethyl ester in the form of a colourless, viscous oil, $n^{24}_D$: 1.5426.

The following are prepared analogously:
From 2-[4-(3-chlorophenoxy)-phenoxy]-ethylcarbamic acid ethyl ester and
a) acetyl chloride, N-acetyl-2-[4-(3-chlorophenoxy)-phenoxy]-ethylcarbamic acid ethyl ester, $n^{20}_D$: 1.5542;
b) chloroformic acid methyl ester, N-methoxycarbonyl-2-[4-(3-chlorophenoxy)-phenoxy]-ethylcarbamic acid ethyl ester, $n^{20}_D$: 1.5493;
c) n-butyric acid chloride, N-(n-butyroyl)-2-[4-(3-chlorophenoxy)-phenoxy]-ethylcarbamic acid ethyl ester, $n^{20}_D$: 1.5469 and
d) dimethylcarbamoyl chloride, N-(dimethylcarbamoyl)-2-[4-(chlorophenoxy)-phenoxy]-ethylcarbamic acid ethyl ester, $n^{21}_D$: 1.5490.

EXAMPLE P7

N-Diethylaminooxalyl-2-[4-(3-chlorophenoxy)phenoxy]-ethylcarbamic acid ethyl ester

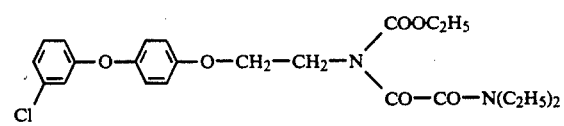

a) 25.4 g of oxalyl chloride are added dropwise at room temperature, with stirring, to a solution of 33.6 g of 2-[4-(3-chlorophenoxy)-phenoxy]-ethylcarbamic acid ethyl ester in 100 ml of 1,2-dichloroethane, and the mixture is heated to reflux temperature and stirred at boiling temperature for a further 4 hours until the evolution of hydrogen chloride gas has ceased. The solvent and the excess oxalyl chloride are then distilled off under a nitrogen atmosphere, and the resulting N-chlorooxalyl-2-[4-(3-chlorophenoxy)-phenoxy]ethylcarbamic acid ethyl ester is freed of gas completely under a high vacuum, $n^{21}_D$: 1.5521.

b) A solution of 4.4 g of diethylamine in 20 ml of toluene is added dropwise at 0° C.-5° C. within a period of 30 minutes, with stirring, to a solution of 8.5 g of N-chlorooxalyl-2-[4-(3-chlorophenoxy)-phenoxy]-ethylcarbamic acid ethyl ester in 80 ml of toluene. The mixture is then stirred at room temperature for 2 hours. The reaction mixture is then washed repeatedly, in succession, with ice-cold 1N hydrochloric acid, with 10% sodium hydrogen carbonate solution and with water, and is then dried over sodium sulfate. The solvent is distilled off completely. Chromatography over silica gel (eluant: n-hexane/diethyl ether, 6:1) yields pure N-(diethylaminooxalyl)-2-[4-(3-chlorophenoxy)-phenoxy]-ethylcarba mic acid ethyl ester, $n^{20}_D$: 1.5471.

The following compounds are prepared analogously to procedure b) from N-chlorooxalyl-2-[4-(3-chlorophenoxy)-phenoxy]-ethylcarbamic acid ethyl ester and morpholine or dibutylamine:
N-(N-morpholinooxalyl)-2-[4-(3-chlorophenoxy)-phenoxy]-ethylcarbamic acid ethyl ester, $n^{21}_D$: 1.5569 and
N-dibutylaminooxalyl-2-[4-(3-chlorophenoxy)-phenoxy]-ethylcarbamic acid ethyl ester, $n^{20}_D$: 1.5345.

The following compounds of formula I can be obtained analogously:

TABLE 1

F—⌬—O—⌬—O—CHR$_4$—CHR$_3$—N(COOR$_1$)(CO—R$_2$) (with F substituent)

| Comp. No. | R$_1$ | R$_2$ | R$_3$ | R$_4$ | Physical Data |
|---|---|---|---|---|---|
| 1.01 | C$_2$H$_5$ | COOC$_2$H$_5$ | H | H | m.p. 73-75° C. |
| 1.02 | C$_2$H$_5$ | COOC$_4$H$_9$-t | H | H | |
| 1.03 | C$_2$H$_5$ | COOCH$_3$ | H | H | m.p. 56-58° C. |
| 1.04 | C$_2$H$_5$ | COOC$_2$H$_5$ | CH$_3$ | H | |
| 1.05 | CH$_3$ | COOCH$_3$ | H | H | |
| 1.06 | C$_3$H$_7$-n | COOC$_2$H$_5$ | H | H | |
| 1.07 | C$_4$H$_9$-n | COOCH$_3$ | H | H | |
| 1.08 | C$_2$H$_5$ | COOCH$_3$ | CH$_3$ | H | |
| 1.09 | C$_2$H$_5$ | COOCH$_3$ | CH$_3$ | CH$_3$ | |

TABLE 1-continued

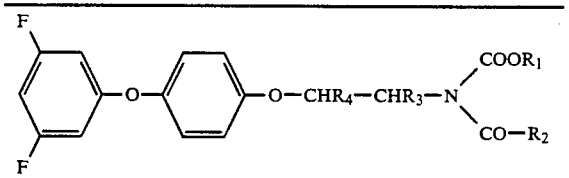

| Comp. No. | R$_1$ | R$_2$ | R$_3$ | R$_4$ | Physical Data |
|---|---|---|---|---|---|
| 1.10 | C$_2$H$_5$ | CH$_3$ | H | H | |
| 1.11 | C$_2$H$_5$ | C$_3$H$_7$-n | H | H | |
| 1.12 | C$_2$H$_5$ | OC$_2$H$_5$ | H | H | |
| 1.13 | C$_2$H$_5$ | OCH$_3$ | H | H | |
| 1.14 | C$_2$H$_5$ | OC$_4$H$_9$-n | H | H | |
| 1.15 | C$_2$H$_5$ | COOC$_8$H$_{17}$-n | H | H | |
| 1.16 | C$_2$H$_5$ | COOC$_3$H$_7$-i | H | H | |
| 1.17 | C$_2$H$_5$ | —N(CH$_3$)$_2$ | H | H | |
| 1.18 | C$_2$H$_5$ | —N(C$_2$H$_5$)$_2$ | H | H | |
| 1.19 | C$_2$H$_5$ | CO—N(C$_2$H$_5$)$_2$ | H | H | |
| 1.20 | C$_2$H$_5$ | CO—N(piperidine) | H | H | |
| 1.21 | C$_2$H$_5$ | CO—N(C$_4$H$_9$-n)$_2$ | H | H | |
| 1.22 | C$_2$H$_5$ | CO—NHC$_4$H$_9$-n | H | H | |
| 1.23 | C$_2$H$_5$ | CO—NH—CH$_2$—C$_6$H$_5$ | H | H | |
| 1.24 | C$_2$H$_5$ | CO—N(morpholine) | H | H | |
| 1.25 | C$_2$H$_5$ | CO—N(CH$_3$)—C$_6$H$_5$ | H | H | |
| 1.26 | C$_2$H$_5$ | CO—NH—C$_6$H$_4$—Cl | H | H | |
| 1.27 | C$_2$H$_5$ | COOC$_2$H$_5$ | H | CH$_3$ | |
| 1.28 | C$_3$H$_7$-i | COOCH$_3$ | H | H | $n_D^{21}$: 1.5152 |
| 1.29 | CH$_3$ | COOC$_2$H$_5$ | H | H | $n_D^{20}$: 1.5230 |

TABLE 2

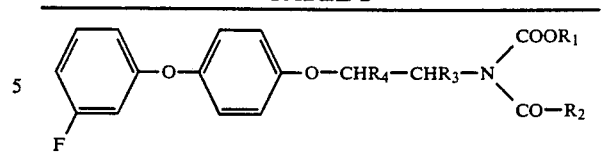

| Comp. No. | R$_1$ | R$_2$ | R$_3$ | R$_4$ | Physical Data |
|---|---|---|---|---|---|
| 2.01 | C$_2$H$_5$ | COOC$_2$H$_5$ | H | H | $n_D^{20}$: 1.5259 |
| 2.02 | C$_2$H$_5$ | COOC$_4$H$_9$-t | H | H | |
| 2.03 | C$_2$H$_5$ | COOCH$_3$ | H | H | |
| 2.04 | C$_2$H$_5$ | COOC$_2$H$_5$ | CH$_3$ | H | |
| 2.05 | CH$_3$ | COOCH$_3$ | H | H | |
| 2.06 | C$_3$H$_7$-n | COOC$_2$H$_5$ | H | H | |
| 2.07 | C$_4$H$_9$-n | COOCH$_3$ | H | H | |
| 2.08 | C$_2$H$_5$ | COOCH$_3$ | CH$_3$ | H | |
| 2.09 | C$_2$H$_5$ | COOCH$_3$ | CH$_3$ | CH$_3$ | |
| 2.10 | C$_2$H$_5$ | CH$_3$ | H | H | |
| 2.11 | C$_2$H$_5$ | C$_3$H$_7$-n | H | H | |
| 2.12 | C$_2$H$_5$ | OC$_2$H$_5$ | H | H | |
| 2.13 | C$_2$H$_5$ | OCH$_3$ | H | H | |
| 2.14 | C$_2$H$_5$ | OC$_4$H$_9$-n | H | H | |
| 2.15 | C$_2$H$_5$ | COOC$_8$H$_{17}$-n | H | H | |
| 2.16 | C$_2$H$_5$ | COOC$_3$H$_7$-i | H | H | |
| 2.17 | C$_2$H$_5$ | —N(CH$_3$)$_2$ | H | H | |
| 2.18 | C$_2$H$_5$ | —N(C$_2$H$_5$)$_2$ | H | H | |
| 2.19 | C$_2$H$_5$ | CO—N(C$_2$H$_5$)$_2$ | H | H | |
| 2.20 | C$_2$H$_5$ | CO—N(piperidine) | H | H | |
| 2.21 | C$_2$H$_5$ | CO—N(C$_4$H$_9$-n)$_2$ | H | H | |
| 2.22 | C$_2$H$_5$ | CO—NHC$_4$H$_9$-n | H | H | |
| 2.23 | C$_2$H$_5$ | CO—NH—CH$_2$—C$_6$H$_5$ | H | H | |
| 2.24 | C$_2$H$_5$ | CO—N(morpholine) | H | H | |
| 2.25 | C$_2$H$_5$ | CO—N(CH$_3$)—C$_6$H$_5$ | H | H | |
| 2.26 | C$_2$H$_5$ | CO—NH—C$_6$H$_5$ | H | H | |
| 2.27 | C$_2$H$_5$ | COOC$_2$H$_5$ | H | CH$_3$ | |

TABLE 3

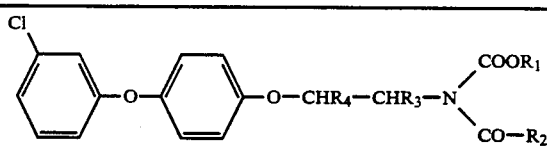

| Comp. No. | R$_1$ | R$_2$ | R$_3$ | R$_4$ | Physical Data |
|---|---|---|---|---|---|
| 3.01 | C$_2$H$_5$ | COOC$_2$H$_5$ | H | H | $n_D^{20}$: 1.5396 |
| 3.02 | C$_2$H$_5$ | COOC$_4$H$_9$-t | H | H | |
| 3.03 | C$_2$H$_5$ | COOCH$_3$ | H | H | $n_D^{21}$: 1.5478 |
| 3.04 | C$_2$H$_5$ | COOC$_2$H$_5$ | CH$_3$ | H | |
| 3.05 | CH$_3$ | COOCH$_3$ | H | H | |
| 3.06 | C$_3$H$_7$-n | COOC$_2$H$_5$ | H | H | |
| 3.07 | C$_4$H$_9$-n | COOCH$_3$ | H | H | |
| 3.08 | C$_2$H$_5$ | COOCH$_3$ | CH$_3$ | H | $n_D^{20}$: 1.5443 |
| 3.09 | C$_2$H$_5$ | COOCH$_3$ | CH$_3$ | CH$_3$ | |
| 3.10 | C$_2$H$_5$ | CH$_3$ | H | H | $n_D^{22}$: 1.5542 |
| 3.11 | C$_2$H$_5$ | C$_3$H$_7$-n | H | H | $n_D^{20}$: 1.5469 |
| 3.12 | C$_2$H$_5$ | OC$_2$H$_5$ | H | H | $n_D^{24}$: 1.5426 |
| 3.13 | C$_2$H$_5$ | OCH$_3$ | H | H | $n_D^{20}$: 1.5493 |
| 3.14 | C$_2$H$_5$ | OC$_4$H$_9$-n | H | H | |
| 3.15 | C$_2$H$_5$ | COOC$_8$H$_{17}$-n | H | H | |
| 3.16 | C$_2$H$_5$ | COOC$_3$H$_7$-i | H | H | |
| 3.17 | C$_2$H$_5$ | —N(CH$_3$)$_2$ | H | H | $n_D^{21}$: 1.5490 |
| 3.18 | C$_2$H$_5$ | —N(C$_2$H$_5$)$_2$ | H | H | |
| 3.19 | C$_2$H$_5$ | CO—N(C$_2$H$_5$)$_2$ | H | H | $n_D^{20}$: 1.5471 |

TABLE 3-continued

[Structure: 3-chlorophenyl-O-phenyl-O-CHR₄-CHR₃-N(COOR₁)(CO-R₂)]

| Comp. No. | R₁ | R₂ | R₃ | R₄ | Physical Data |
|---|---|---|---|---|---|
| 3.20 | $C_2H_5$ | CO—N(piperidinyl) | H | H | |
| 3.21 | $C_2H_5$ | CO—N($C_4H_9$-n)$_2$ | H | H | $n_D^{20}$: 1.5345 |
| 3.22 | $C_2H_5$ | CO—NH$C_4H_9$-n | H | H | |
| 3.23 | $C_2H_5$ | CO—NH—$CH_2$—$C_6H_5$ | H | H | |
| 3.24 | $C_2H_5$ | CO—N(morpholinyl) | H | H | $n_D^{21}$: 1.5569 |
| 3.25 | $C_2H_5$ | CO—N($CH_3$)—$C_6H_5$ | H | H | |
| 3.26 | $C_2H_5$ | CO—NH—$C_6H_5$ | H | H | |
| 3.27 | $C_2H_5$ | COO$C_2H_5$ | H | $CH_3$ | $n_D^{20}$: 1.5303 |
| 3.28 | $C_2H_5$ | COO$C_8H_{17}$-n | H | H | $n_D^{25}$: 1.5229 |
| 3.29 | $CH_2CH=CH_2$ | COO$C_2H_5$ | H | H | $n_D^{20}$: 1.5441 |

TABLE 4

[Structure: 2,5-dichlorophenyl-O-phenyl-O-CHR₄-CHR₃-N(COOR₁)(CO-R₂)]

| Comp. No. | R₁ | R₂ | R₃ | R₄ | Physical Data |
|---|---|---|---|---|---|
| 4.01 | $C_2H_5$ | COO$CH_3$ | H | H | $n_D^{20}$: 1.5512 |
| 4.02 | $C_2H_5$ | COO$C_2H_5$ | H | H | |
| 4.03 | $C_2H_5$ | $CH_3$ | H | H | |
| 4.04 | $C_2H_5$ | $C_3H_7$-n | H | H | |
| 4.05 | $C_2H_5$ | O$C_2H_5$ | H | H | |
| 4.06 | $C_2H_5$ | N($C_2H_5$)$_2$ | H | H | |
| 4.07 | $C_2H_5$ | COO$C_2H_5$ | $CH_3$ | H | |
| 4.08 | $C_2H_5$ | $CH_3$ | $CH_3$ | H | |
| 4.09 | $C_2H_5$ | COO$C_2H_5$ | $CH_3$ | $CH_3$ | |

Formulation Examples for liquid active ingredients of formula I (throughout, percentages are by weight)

| F1. Emulsifiable concentrates | a) | b) | c) |
|---|---|---|---|
| compound 1.05 | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexanone | — | 15% | 20% |
| xylene mixture | 65% | 25% | 20% |

Emulsions of any desired concentration can be produced from such concentrates by dilution with water.

| F2. Solutions | a) | b) | c) | d) |
|---|---|---|---|---|
| compound no. 3.01 | 80% | 10% | 5% | 95% |
| ethylene glycol monomethyl ether | 20% | — | — | — |
| polyethylene glycol (mol. wt. 400) | — | 70% | — | — |
| N-methyl-2-pyrrolidone | — | 20% | — | — |
| epoxidised coconut oil | — | — | 1% | 5% |
| ligroin (boiling range 160-190° C.) | — | — | 94% | — |

The solutions are suitable for application in the form of micro-drops.

| F3. Granulates | a) | b) |
|---|---|---|
| compound no. 3.10 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| F4. Dusts | a) | b) |
|---|---|---|
| compound no. 4.01 | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

Formulation Examples for solid active ingredients of formula I (throughout, percentages are by weight)

| F5. Wettable powders | a) | b) | c) |
|---|---|---|---|
| compound no. 1.01 or 1.03 | 25% | 50% | 75% |
| sodium lignosulfonate | 5% | 5% | — |

| F5. Wettable powders | a) | b) | c) |
|---|---|---|---|
| sodium laurylsulfate | 3% | — | 5% |
| sodium diisobutylnaphthalene-sulfonate | — | 6% | 10% |
| octylphenol polyethylene glycol ether (7-8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| F6. Emulsifiable concentrate | |
|---|---|
| compound no. 1.01 or 1.03 | 10% |
| octylphenol polyethylene glycol ether (4-5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| F7. Dusts | a) | b) |
|---|---|---|
| compound no. 1.01 or 1.03 | 5% | 8% |
| talcum | 95% | — |
| kaolin | — | 92% |

Ready-for-use dusts are obtained by mixing the active ingredient with the carrier and grinding the mixture in a suitable mill.

| F8. Extruder granulate | |
|---|---|
| compound no. 1.01 or 1.03 | 10% |
| sodium lignosulfonate | 2% |
| carboxymethylcellulose | 1% |
| kaolin | 87% |

The active ingredient is mixed and ground with the adjuvants, and the mixture is moistened with water. The mixture is extruded, granulated and then dried in a stream of air.

| F9. Coated granulate | |
|---|---|
| compound no. 1.03 | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granulates are obtained in this manner.

| F10. Suspension concentrate | |
|---|---|
| compound no. 1.03 | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

In the following biological Examples, good activity means that the desired effect occurs to an extent of at least from 50 to 60%.

EXAMPLE B1

Action against *Dermanyssus gallinae*

2 to 3 ml of a solution containing 10 ppm of test compound, and approximately 200 mites at various stages of development, are placed in a glass container that is open at the top. The container is then closed with a cotton wool plug, shaken for 10 minutes until the mites are completely wetted, and then inverted for a short time so that the remaining test solution can be absorbed by the cotton wool. After 3 days, the mortality of the mites is determined as a percentage by counting the number of dead individuals.

Compounds of Tables 1, 2, 3 and 4 exhibit good activity against Dermanyssus gallinae.

EXAMPLE B2

Action against *Boophilus microplus*

Adult female ticks which are replete with blood are affixed to a PVC plate and covered with a cotton wool swab. For treatment, 10 ml of an aqueous solution containing 125 ppm of the test compound are poured over the test insects. The cotton wool swab is then removed and the ticks are incubated for 4 weeks until oviposition has taken place. The action against Boophilus microplus manifests itself either as mortality or sterility of the females or as ovicidal action in the eggs.

In this test, compounds of Tables 1, 2, 3 and 4 exhibit good activity against Boophilus microplus. In particular, compounds 1.01, 1.03, 3.01, 3.10, 3.12 and 3.17 are more than 80% effective.

EXAMPLE B3

Ovicidal action against *Cydia pomonella*

Egg deposits of *Cydia pomonella* on filter paper are immersed for a short time in an aqueous acetone solution of the test compound having a concentration of 400 ppm. After the test solution has dried, the eggs are incubated in petri dishes. After 6 days, the percentage of eggs which have hatched is evaluated in comparison with untreated controls (% reduction in hatching rate).

Compounds of Table 1 exhibit good activity against *Cydia pomonella* in this test. In particular, compounds 1.01, 1.03, 1.05, 3.01, 3.03, 3.12, 3.13 and 3.17 are more than 80% effective.

EXAMPLE B4

Ovicidal action against *Adoxophyes reticulana*

Egg deposits of *Adoxophyes reticulana* on filter paper are immersed for a short time in an aqueous acetone solution of the test compound having a concentration of 400 ppm. After the test solution has dried, the eggs are incubated in petri dishes. After 6 days, the percentage of eggs which have hatched is evaluated in comparison with untreated controls (% reduction in hatching rate).

Compounds of Tables 1, 2, 3 and 4 exhibit good activity against *Adoxophyes reticulana* in this test. In particular, compounds 1.01, 1.03, 1.05, 3.01, 3.03, 3.12, 3.13 and 3.17 are more than 80% effective.

EXAMPLE B5

Ovicidal action against *Lobesia botrana*

Egg deposits of *Lobesia botrana* on filter paper are immersed for a short time in an aqueous acetone solution of the test compound having a concentration of 400 ppm. After the test solution has dried, the eggs are incubated in petri dishes. After 6 days, the percentage of eggs which have hatched is evaluated in comparison with untreated controls (% reduction in hatching rate).

Compounds of Tables 1, 2, 3 and 4 exhibit good activity against *Lobesia botrana* in this test. In particular, compounds 1.01 and 1.03 are more than 80% effective.

EXAMPLE B6

Ovicidal action against *Heliothis virescens*

Egg deposits of *Heliothis virescens* on filter paper are immersed for a short time in an aqueous acetone solution of the test compound having a concentration of 400 ppm. After the test solution has dried, the eggs are incubated in petri dishes. After 6 days, the percentage of eggs which have hatched is evaluated in comparison with untreated controls (% reduction in hatching rate).

Compounds of Tables 1, 2, 3 and 4 exhibit good activity against *Heliothis virescens* in this test. In particular, compounds 1.01, 1.03 and 3.10 are more than 80% effective.

EXAMPLE B7

Action against *Aonidiella aurantii*

Potato tubers are populated with crawlers of *Aonidiella aurantii* (red citrus scale). After about 2 weeks, the potatoes are immersed in an aqueous emulsion or suspension containing the test compound in a concentration of 400 ppm. After the treated potato tubers have dried, they are incubated in a plastics container. Evaluation is made 10-12 weeks later by comparing the survival rate of the crawlers of the first subsequent generation of the treated scale population with that of untreated controls.

Compounds of Tables 1, 2, 3 and 4 exhibit good activity against *Aonidiella aurantii* in this test.

EXAMPLE B8

Action against *Nilaparvata lugens*

Rice plants are sprayed with an aqueous emulsion containing 400 ppm of test compound. After the spray coating has dried, the rice plants are populated with cicada larvae in the 2nd and 3rd stages. Evaluation is made 21 days later. The percentage reduction in the population (% activity) is determined by comparing the number of surviving cicadas on the treated plants with that on untreated plants.

The compounds of Tables 1, 2, 3 and 4 exhibit good activity against *Nilaparvata lugens* in this test. In particular, compounds 1.01, 1.03, 1.05, 3.01, 3.03, 3.10, 3.11, 3.12, 3.13 and 3.17 are more than 80% effective.

EXAMPLE B9

Action against *Nephotettix cincticeps*

Rice plants are sprayed with an aqueous emulsion containing 400 ppm of test compound. After the spray coating has dried, the rice plants are populated with cicada larvae in the 2nd and 3rd stages. Evaluation is made 21 days later. The percentage reduction in the population (% activity) is determined by comparing the number of surviving cicadas on the treated plants with that on untreated plants.

The compounds of Tables 1, 2, 3 and 4 exhibit good activity against *Nephotettix cincticeps* in this test. In particular, compounds 1.01, 1.03, 1.05, 3.01, 3.03, 3.10, 3.11, 3.12, 3.13 and 3.17 are more than 80% effective.

EXAMPLE B10

Action against *Bemisia tabaci*

Dwarf bean plants are placed in gauze cages and populated with adults of Bemisia tabaci (whitefly). After oviposition has taken place, all adults are removed and 10 days later the plants and the nymphs located thereon are sprayed with an aqueous emulsion of the test compounds (concentration 400 ppm). Evaluation is made 14 days after application of the test compound by determining the percentage hatching rate in comparison with untreated controls.

The compounds of Tables 1, 2, 3 and 4 exhibit good activity in this test. Compounds 1.01, 1.03, 1.05 and 3.03 are still 80% effective at concentrations of 10 ppm.

EXAMPLE B11

Ovicidal/larvicidal action against *Heliothis virescens*

Egg deposits of *Heliothis virescens* on cotton are sprayed with an aqueous emulsion containing 400 ppm of test compound. 8 days later, the percentage of eggs which have hatched and the survival rate of the caterpillars are evaluated in comparison with untreated controls (% reduction in the population).

Compounds of Tables 1, 2, 3 and 4 exhibit good activity against *Heliothis virescens* in this test. In particular, compounds 1.01, 1.03, 1.05, 3.01, 3.03, 3.11, 3.13 and 3.17 are more than 80% effective.

What is claimed is:

1. N-Acyl-2-[4-(halophenoxy)-phenoxy]-ethylcarbamic acid esters of formula I

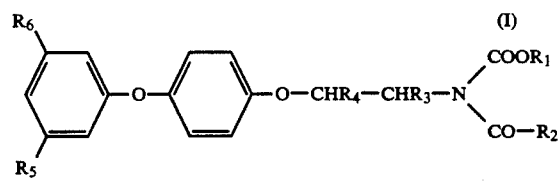

wherein
$R_1$ is $C_1$–$C_8$alkyl or $C_3$–$C_5$alkenyl,
$R_2$ is $C_1$–$C_8$alkyl, $C_1$–$C_8$alkoxy, —CO—$R_7$ or —$NR_8R_9$,
$R_3$ and $R_4$ independently of one another are hydrogen or methyl,
$R_5$ is chlorine or fluorine,
$R_6$ is either the same substituent as $R_5$ or is hydrogen,
$R_7$ is $C_1$–$C_8$alkoxy or —$NR_{10}R_{11}$,
$R_8$ is $C_1$–$C_4$alkyl,
$R_9$ is $C_1$–$C_4$alkyl or R₈ and R₉ together form a C₄-C₆alkylene chain which may be interrupted by oxygen, sulfur or —NCH₃—, R₁₀ is hydrogen or C₁-C₄alkyl and R₁₁ is hydrogen or C₁-C₄alkyl, benzyl, phenyl, or phenyl substituted by halogen or by methyl, or R₁₀ and R₁₁ together form a C₄-C₆alkylene chain which may be interrupted by oxygen, sulfur or —NCH₃—.

2. A compound according to claim 1, wherein R₁ is C₁-C₄alkyl, R₂ is C₁-C₄alkyl, C₁-C₄alkoxy, C₁-C₄alkoxycarbonyl, C₁-C₄dialkylamino or —CONR₁₀R₁₁, and R₅ and R₆ are both either fluorine or chlorine, or R₅ is chlorine or fluorine and R₆ is hydrogen, wherein R₁₀ is hydrogen or C₁-C₄alkyl and R₁₁ is hydrogen, C₁-C₄alkyl or phenyl, or R₁₀ and R₁₁ together form a C₄-C₆alkylene chain which may be interrupted by oxygen.

3. A compound according to claim 2, wherein R₂ is C₁-C₄alkyl, C₁-C₄alkoxy, C₁-C₄alkoxycarbonyl, C₁-C₂dialkylamino, di(C₁-C₄alkyl)-aminocarbonyl or C₄-C₆alkyleneaminocarbonyl.

4. A compound according to claim 1, wherein R₁ is C₁-C₄alkyl, R₂ is C₁-C₄alkyl, C₁-C₄alkoxy, di-(C₁-C₂alkyl)-aminocarbonyl or C₁-C₄alkoxycarbonyl, R₃ is methyl or hydrogen, R₄ is hydrogen, and R₅ and R₆ are fluorine or chlorine.

5. A compound according to claim 1 selected from the group

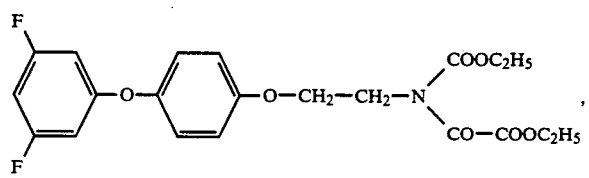

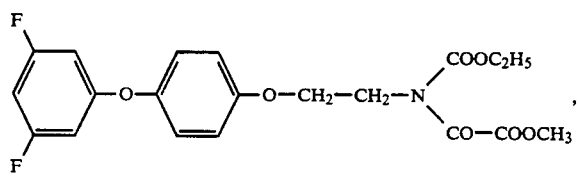

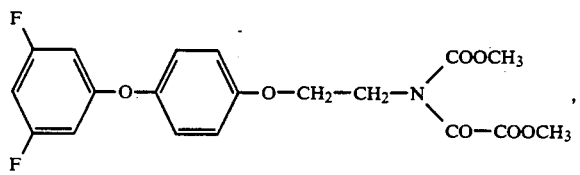

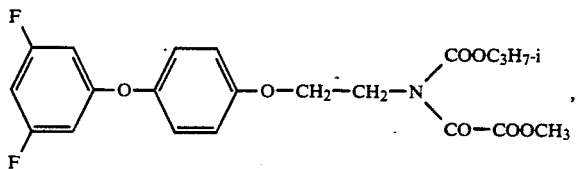

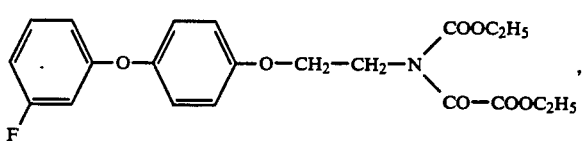

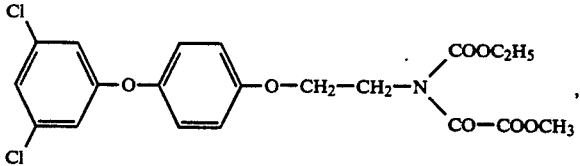

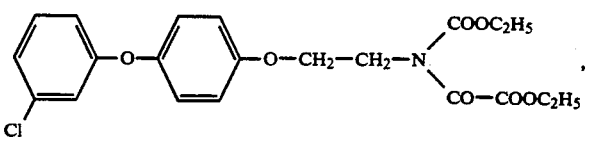

-continued
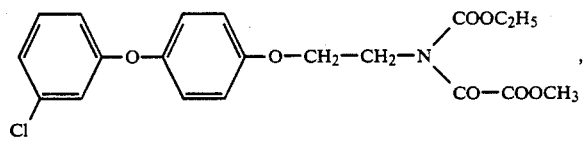
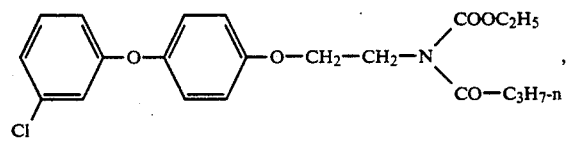
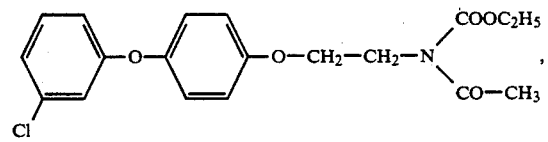
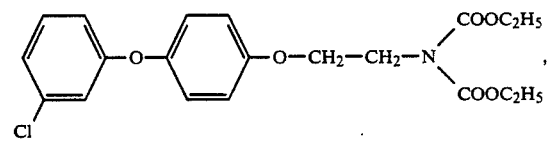
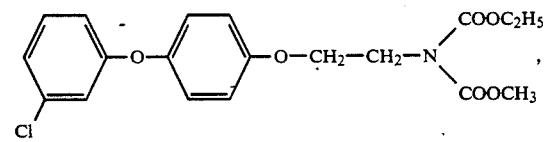
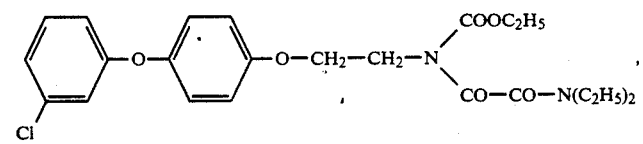
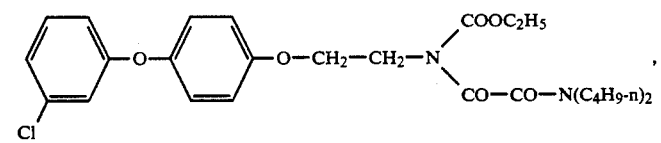
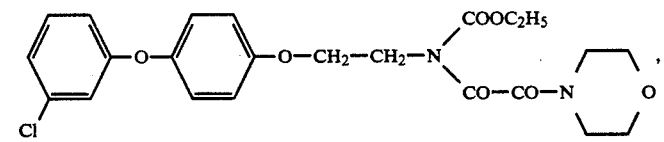
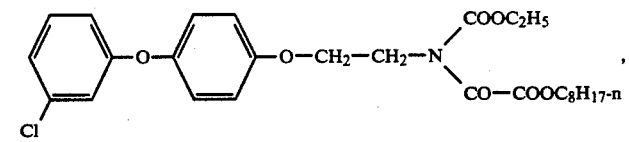
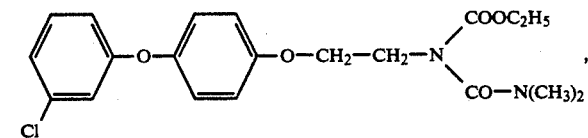

[Structures at top:]

3-Cl-C6H4-O-C6H4-O-CH2-CH2-N(COOCH2-CH=CH2)(CO-COOC2H5)

3-Cl-C6H4-O-C6H4-O-CH2-CH(CH3)-N(COOC2H5)(CO-COOC2H5)   and

3-Cl-C6H4-O-C6H4-O-CH(CH3)-CH2-N(COOC2H5)(CO-COOC2H5)

6. A pesticidal composition, which contains as active ingredient at least one compound of formula I $$\text{R}_6\text{-C}_6\text{H}_3(\text{R}_5)\text{-O-C}_6\text{H}_4\text{-O-CHR}_4\text{-CHR}_3\text{-N(COOR}_1)(\text{CO-R}_2)$$  (I)

wherein
$R_1$ is $C_1$-$C_8$alkyl or $C_3$-$C_5$alkenyl,
$R_2$ is $C_1$-$C_8$alkyl, $C_1$-$C_8$alkoxy, —CO—$R_7$ or —NR$_8$R$_9$,
$R_3$ and $R_4$ independently of one another are hydrogen or methyl,
$R_5$ is chlorine or fluorine,
$R_6$ is either the same substituent as $R_5$ or is hydrogen,
$R_7$ is $C_1$-$C_8$alkoxy or —NR$_{10}$R$_{11}$,
$R_8$ is $C_1$-$C_4$alkyl,
$R_9$ is $C_1$-$C_4$alkyl or
$R_8$ and $R_9$ together form a $C_4$-$C_6$alkylene chain which may be interrupted by oxygen, sulfur or —NCH$_3$—,
$R_{10}$ is hydrogen or $C_1$-$C_4$alkyl and
$R_{11}$ is hydrogen or $C_1$-$C_4$alkyl, benzyl, phenyl, or phenyl substituted by halogen or by methyl, or
$R_{10}$ and $R_{11}$ together form a $C_4$-$C_6$alkylene chain which may be interrupted by oxygen, sulfur or —NCH$_3$— and a carrier.

7. A method of controlling arthropodal pests on plants or animals or in the home, which comprises contacting said pests or their habitat with an arthopodicidally effective amount of a compound of formula I $$\text{R}_6\text{-C}_6\text{H}_3(\text{R}_5)\text{-O-C}_6\text{H}_4\text{-O-CHR}_4\text{-CHR}_3\text{-N(COOR}_1)(\text{CO-R}_2)$$  (I)

wherein
$R_1$ is $C_1$-$C_8$alkyl or $C_3$-$C_5$alkenyl,
$R_2$ is $C_1$-$C_8$alkyl, $C_1$-$C_8$alkoxy, —CO—$R_7$ or —NR$_8$R$_9$,
$R_3$ and $R_4$ independently of one another are hydrogen or methyl,
$R_5$ is chlorine or fluorine,
$R_6$ is either the same substituent as $R_5$ or is hydrogen,
$R_7$ is $C_1$-$C_8$alkoxy or —NR$_{10}$R$_{11}$,
$R_8$ is $C_1$-$C_4$alkyl,
$R_9$ is $C_1$-$C_4$alkyl or
$R_8$ and $R_9$ together form a $C_4$-$C_6$alkylene chain which may be interrupted by oxygen, sulfur or —NCH$_3$—,
$R_{10}$ is hydrogen or $C_1$-$C_4$alkyl and
$R_{11}$ is hydrogen or $C_1$-$C_4$alkyl, benzyl, phenyl, or phenyl substituted by halogen or by methyl, or
$R_{10}$ and $R_{11}$ together form a $C_4$-$C_6$alkylene chain which may be interrupted by oxygen, sulfur or —NCH$_3$—.

8. A method according to claim 7 for controlling arthropods, selected from insects and arachnids.

9. A method according to claim 8 for controlling larvae or eggs of phytophagous insect or mite pests.

* * * * *